United States Patent
Yang

(10) Patent No.: US 9,526,485 B2
(45) Date of Patent: Dec. 27, 2016

(54) DEVICE OF AUTOMATIC MECHANICAL WOUND OPENER FOR HEAD AND NECK SURGERY

(71) Applicant: National Taiwan University Hospital, Taipei (TW)

(72) Inventor: Tsung-Lin Yang, Taipei (TW)

(73) Assignee: NATIONAL TAIWAN UNIVERSITY HOSPITAL, Taipei (TW)

( * ) Notice: Subject to any disclaimer, the term of this patent is extended or adjusted under 35 U.S.C. 154(b) by 103 days.

(21) Appl. No.: 14/047,104

(22) Filed: Oct. 7, 2013

(65) Prior Publication Data

US 2015/0100078 A1    Apr. 9, 2015

(51) Int. Cl.
*A61B 1/32* (2006.01)
*A61B 17/02* (2006.01)

(52) U.S. Cl.
CPC .......... *A61B 17/0206* (2013.01); *A61B 90/50* (2016.02); *A61B 2090/571* (2016.02)

(58) Field of Classification Search
CPC . A61B 17/02; A61B 17/0206; A61B 17/0218; A61B 90/50

USPC ................... 600/201–203, 210–246
See application file for complete search history.

(56) References Cited

U.S. PATENT DOCUMENTS

| | | | |
|---|---|---|---|
| 4,989,587 A * | 2/1991 | Farley | A61B 17/0206 600/228 |
| 7,654,954 B1 * | 2/2010 | Phillips et al. | 600/228 |
| 2009/0287062 A1 * | 11/2009 | Farley | 600/231 |

* cited by examiner

*Primary Examiner* — Kevin T Truong
*Assistant Examiner* — Si Ming Ku
(74) *Attorney, Agent, or Firm* — Muncy, Geissler, Olds & Lowe, P.C.

(57) ABSTRACT

A wound opener is provided. An operative field can be created through head/neck soft tissues for introducing the endoscopes and robotic surgical tools. An incision size can be properly adjusted. Thus, endoscopes, robotic arms or other devices can be smoothly introduced into the operative field to evaluate and treat lesions of head and neck soft tissues. Hence, the present invention facilitates surgical procedure, reduces wound size and effectively conceals wound to make it become invisible.

5 Claims, 5 Drawing Sheets

DEVICE OF AUTOMATIC MECHANICAL WOUND OPENER FOR HEAD AND NECK SURGERY

TECHNICAL FIELD OF THE INVENTION

The present invention relates to creating a wound opener for head and neck surgery; more particularly, relates to using an automatic mechanic wound opener to control the position and size of a wound for head and neck surgery and to introduce endoscopes or robotic arms through the wound to evaluate and further treat lesions of head and neck, where the surgery can be performed smoothly, the wound size can be reduced, and the wound can be effectively concealed and become invisible.

DESCRIPTION OF THE RELATED ART

Head/neck surgery is usually performed by an open operation. An incision made at head/neck and soft tissues are pulled outwardly for treating lesions. Hence, the traditional head/neck surgery may result in an obvious visible wound. Furthermore, the issues pertinent to postoperative care and cosmetic results of the wound are also encountered.

Endoscopes or robotic arms can be used for solving these problems. During the surgery, an operative space is required to be created at first for smoothly introducing the endoscopes or robotic arms to evaluate and further treat lesions. The head and neck of a human body has many different perplexing soft tissues, like muscles, nerves, glands and vessels. In addition, head and neck have smaller spaces than the other parts of the body for dissection. Until now, no proper wound opener is available for head and neck surgery when the endoscopes or robotic arms are used. As a result, the endoscopes or robotic arms cannot be operated easily, which makes surgical procedures difficult.

Hence, the prior art does not fulfill all users' requests on actual use.

SUMMARY OF THE INVENTION

The main purpose of the present invention is to use a mechanic wound opener to adjust the position and size of a wound for introducing endoscopes or robotic arms to evaluate and further treat lesions of head and neck, where surgery can be performed smoothly, the wound size can be reduced and the wound can be effectively concealed and become invisible.

To achieve the above purpose, the present invention is a device of automatic mechanical wound opener for head and neck surgery, comprising an operating frame and a wound opener, where the wound opener is set at an end of the operating frame; the wound opener comprises a fixed unit and a drawing unit; the drawing unit is movably located on the fixed unit; the supporting unit comprises an adjusting base and a vertical rod set on the adjusting base; the connecting unit comprises a second adjusting base movably set on the vertical rod and a horizontal rod set on the second adjusting base; the fixed unit comprises an adjusting unit set at an end of the horizontal rod and a plurality of moving track rods movably set in the adjusting unit; the drawing unit includes a blade separately located at an end of each moving track rod; the vertical adjusting plate is set on at least one of the moving track rods; one of the blades is connected to the vertical adjusting plate; the adjusting unit has a chute to be movably combined with the moving track rods; and each moving track rod has a locking unit to be movably combined with one of the blades. Accordingly, a novel device of automatic mechanical wound opener for head and neck surgery is obtained.

BRIEF DESCRIPTIONS OF THE DRAWINGS

The present invention will be better understood from the following detailed description of the preferred embodiment according to the present invention, taken in conjunction with the accompanying drawings, in which FIG. 1 is the perspective view showing the preferred embodiment according to the present invention;

DESCRIPTION OF THE PREFERRED EMBODIMENT

The following description of the preferred embodiment is provided to understand the features and the structures of the present invention.

Figure 1:
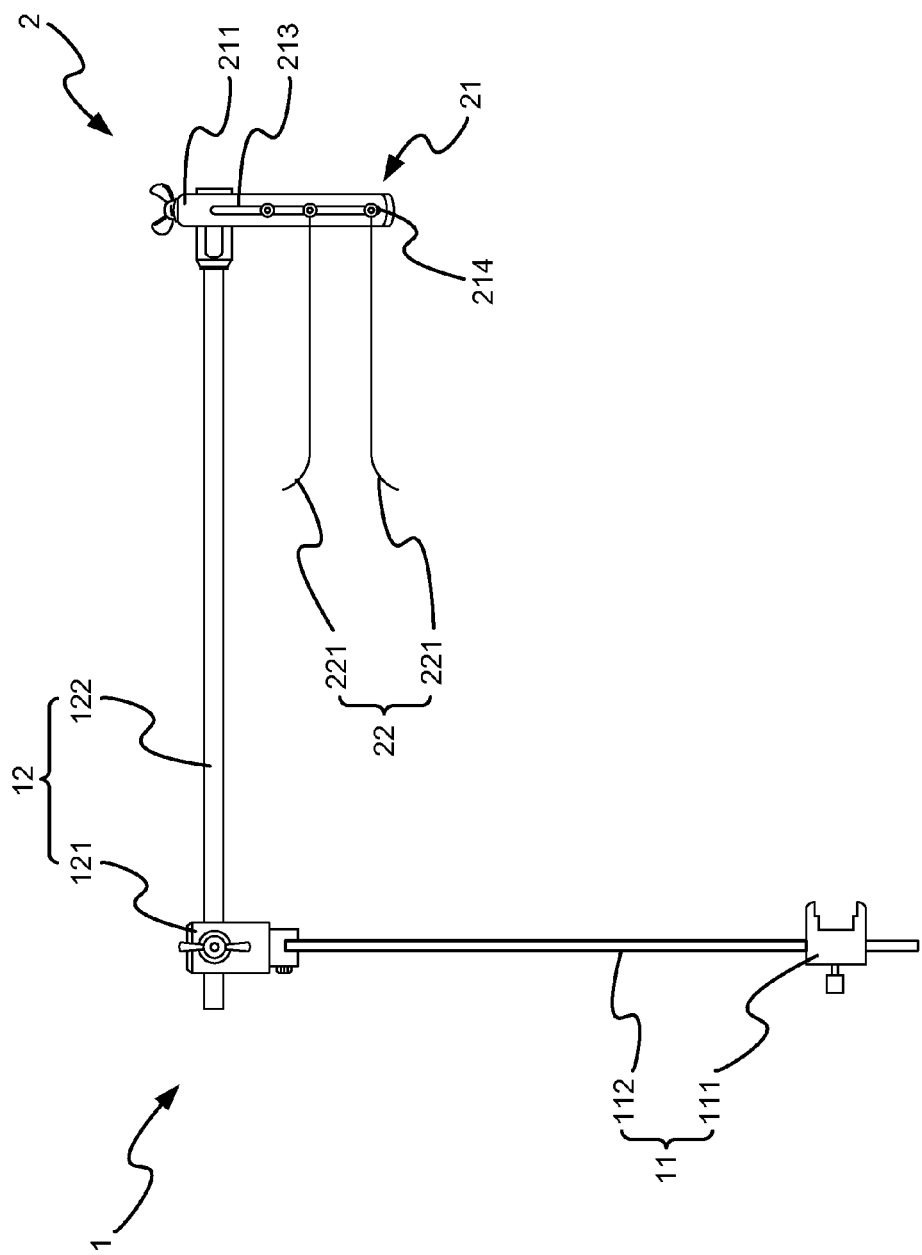
Figure 2:
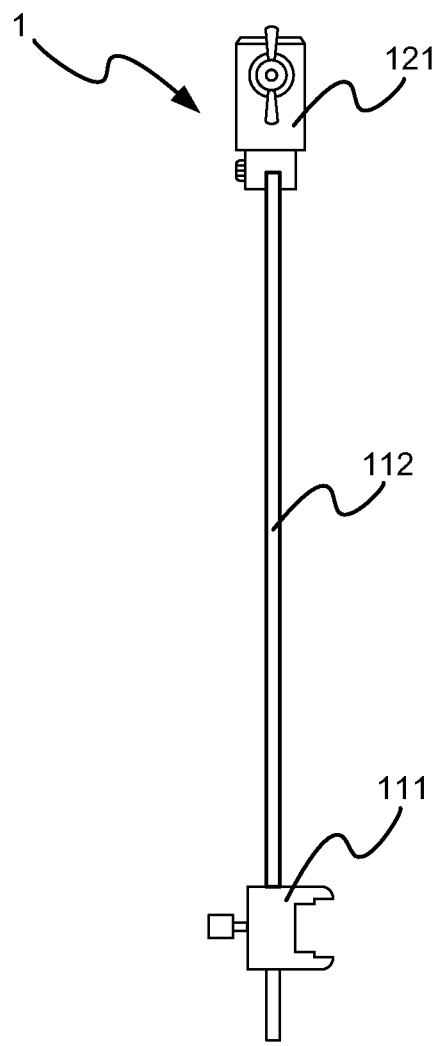
FIG. 2 is the side view showing the preferred embodiment.
Figure 3:
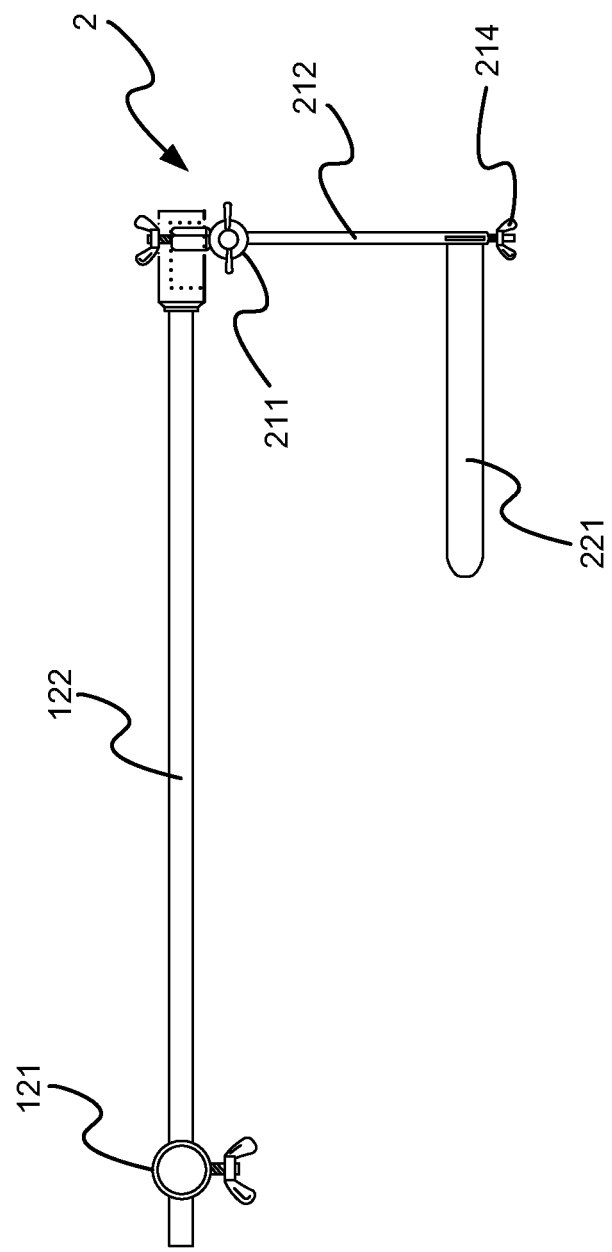
FIG. 3 is the top-down view showing the preferred embodiment.
Figure 4:
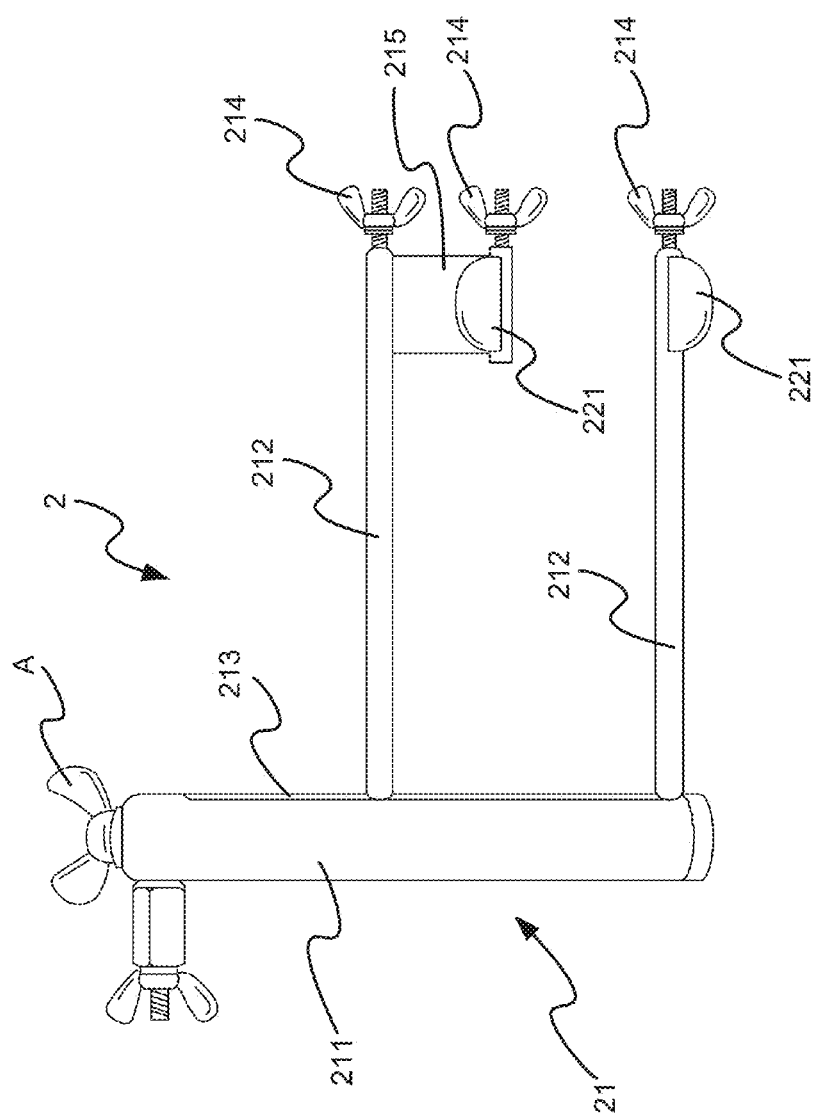
FIG. 4 is the perspective view showing the wound opener.
Figure 5:
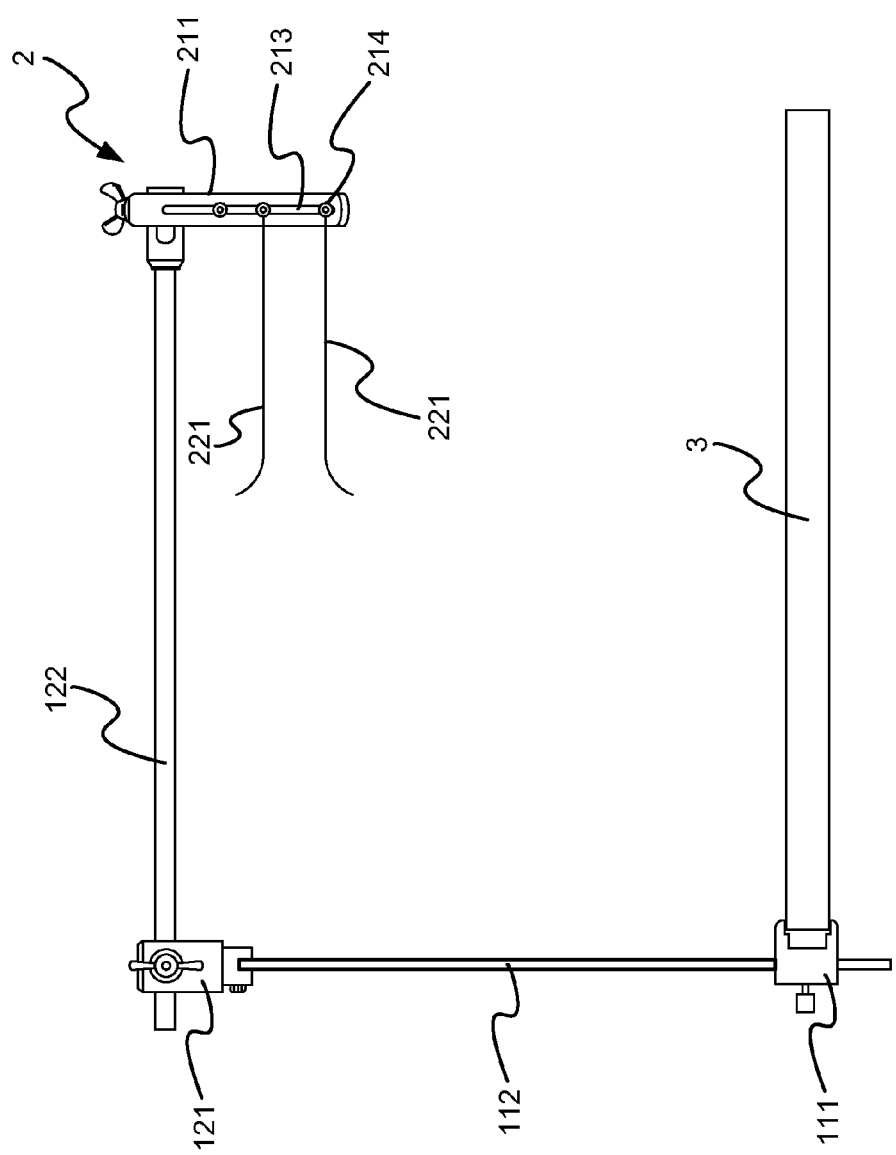
FIG. 5 is the view showing the state of use of the preferred embodiment.

Please refer to FIG. 1 to FIG. 5, which are a perspective view, a side view and a top-down view showing a preferred embodiment according to the present invention; a perspective view showing the wound opener; and a view showing a state of use of the preferred embodiment. As shown in the figures, the present invention is a device of automatic mechanical wound opener for head and neck surgery, comprising an operating frame 1 and a wound opener 2.

The operating frame 1 comprises a supporting unit 11; and a connecting unit 12 movably connected with the supporting unit 11, where the supporting unit 11 comprises a first adjusting base 111 and a vertical rod 112 set on the first adjusting base 111; and the connecting unit 12 comprises a second adjusting base 121 movably set on the vertical rod 112 and a horizontal rod 122 set on the second adjusting base 121.

The wound opener 2 is set at an end of the horizontal rod 122 of the connecting unit 12 of the operating frame 1. Therein, the wound opener 2 comprises a fixed unit 21 and a drawing unit 22 movably set on the fixed unit 21; the fixed unit 21 comprises an adjusting unit 211 with actuator A set at an end of the horizontal rod 122 and a plurality of moving track rods 212 movably set in the adjusting unit 211; the drawing unit 22 includes a blade 221 separately set at an end of each one of the moving track rods 212; the adjusting unit 211 is set with a chute 213 for movably combining the moving track rods 212; each moving track rod 212 is separately set with a locking unit 214 for movably combined with the blade 221; a vertical adjusting plate 215 is set on at least one moving track rod 212 (at an upper side); and, one blade 221 (the blade at the upper side) is connected with the vertical adjusting plate 215.

Thus, a novel device of automatic mechanical wound opener of head/neck soft tissues is obtained.

Using the present invention, the first adjusting base 111 of the supporting unit 11 of the operating frame 1 is set at a side of an operating bed 3 to establish the wound opener 2. A height of the vertical rod 112 and a fixed position of the vertical rod 112 corresponding to the operating bed 3 are adjusted before setting the first adjusting base 111. In addition, an operational length of the horizontal rod 122 is adjusted by the second adjusting base 121 before being fixed for adjusting the wound opener 2 according to a patient's position. Thus, the operating frame 1 and the wound opener 2 are fixed on the operating bed 3 for preventing sway during surgery.

After the supporting unit 11 and the connecting unit 12 of the operating frame 1 are adjusted to proper positions, the drawing unit 22 of the wound opener 2 is set at a wound on skin of the patient for surgery and each blade 221 is introduced into the wound from outward to inward for hooking head/neck soft tissues at upper and lower sides. The blade 221 moves with the moving track rod 212 within the chute 213 via operation of the actuator A of the adjusting unit 211; or, the vertical adjusting plate 215 is used to adjust the position of the blade 221 at the upper side. After each blade 221 is moved to a fixed position, the adjusting unit 211 is fixed to decide wound size, where each blade 221 is adjusted to create a sufficient operative space and to be fixed for maintaining the space. Thus, each blade 221 is used to create the operative space, where endoscopes or robotic arms can be smoothly introduced to evaluate and treat lesions. The wound opener 2 helps operators (doctors) on head and neck surgeries, where the wound size can be further reduced and the wound can be effectively concealed.

During practical use, each blade 221 can be changed based on different requirement. For changing the blade 221, the locking unit 214 at the end of the moving track rod 212 is removed; then, the original blade 221 on the moving track rod 212 is taken off; then, a proper blade is re-set on the moving track rod 212; and, then, the locking unit 214 is locked at the end of the moving track rod 212. Thus, the blade 221 is changed to meet special needs of distinct situations.

To sum up, the present invention is a device of automatic mechanical wound opener for head and neck surgery, where a mechanic wound opener is used to adjust position and size of a wound for introducing endoscopes or robotic arms to evaluate and treat head and neck lesions; and, thus, the present invention facilitates surgical procedure, reduces wound size and effectively conceals the wound to make it become invisible.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A device of automatic mechanical wound opener for head and neck surgery, comprising:
   an operating frame comprising a connecting unit; and
   a wound opener, said wound opener being located at an end of said operating frame, said wound opener comprising:
   a fixed unit; and
   a drawing unit, said drawing unit being movably located on said fixed unit,
   wherein said fixed unit of said wound opener comprises an adjusting unit and a plurality of moving track rods,
   wherein said adjusting unit is located at an end of a horizontal rod of said connecting unit,
   wherein said moving track rods are vertically movably located in said adjusting unit,
   wherein said drawing unit includes a plurality of blades respectively directly or indirectly connected to an end of each one of said moving track rods,
   wherein one end of a vertical adjusting plate is connected to at least one of said moving track rods, one of the blades is connected to the other end of said vertical adjusting plate, the remaining blades are directly connected to each of said moving track rods, respectively, whereby reducing a distance between said blade connecting to said vertical adjusting plate and the neighboring blade next to the other end of said vertical adjusting plate, and
   wherein said vertical adjusting plate is disposed between said at least one of said moving track rods and said at least one of said blades.

2. The device according to claim 1, wherein said operating frame further comprises a supporting unit; said connecting unit is movably combined with said supporting unit; and said wound opener is located at an end of said connecting unit.

3. The device according to claim 2, wherein said supporting unit comprises an adjusting base and a vertical rod and said vertical rod is located on said adjusting base.

4. The device according to claim 3, wherein said connecting unit comprises a second adjusting base and said horizontal rod; said second adjusting base is movably located on said vertical rod; said horizontal rod is located on said second adjusting base; and said horizontal rod is perpendicular to said vertical rod.

5. The device according to claim 1, wherein said adjusting unit has a chute to be movably combined with said moving track rods; and each moving track rod has a locking unit to be movably combined with one of said blades.

* * * * *